(12) United States Patent
Wu et al.

(10) Patent No.: US 10,278,636 B2
(45) Date of Patent: May 7, 2019

(54) NEAR-INFRARED SPECTRUM IMAGING SYSTEM AND METHOD FOR DIAGNOSIS OF DEPTH AND AREA OF BURN SKIN NECROSIS

(71) Applicant: CHONGQING SOUTHWEST HOSPITAL, Chongqing (CN)

(72) Inventors: Jun Wu, Chongqing (CN); Cangli Liu, Mianyang (CN); Junjie Yang, Chongqing (CN); Yongquan Luo, Mianyang (CN); Lixian Huang, Mianyang (CN); Gaoxing Luo, Chongqing (CN); Zhiqiang Chen, Chongqing (CN); Jianheng Zhao, Mianyang (CN); Dayong Zhang, Mianyang (CN); Zhixue Shen, Mianyang (CN); Jianfeng Li, Mianyang (CN); Weifeng He, Mianyang (CN)

(73) Assignee: BEIJING HEFENGLIANKANG INVESTMENT MANAGEMENT LTD, Beijing (CN)

( * ) Notice: Subject to any disclaimer, the term of this patent is extended or adjusted under 35 U.S.C. 154(b) by 255 days.

(21) Appl. No.: 15/114,794

(22) PCT Filed: Jan. 9, 2015

(86) PCT No.: PCT/CN2015/070456
§ 371 (c)(1),
(2) Date: Jul. 27, 2016

(87) PCT Pub. No.: WO2015/113460
PCT Pub. Date: Aug. 6, 2015

(65) Prior Publication Data
US 2016/0345888 A1     Dec. 1, 2016

(30) Foreign Application Priority Data
Jan. 28, 2014   (CN) .......................... 2014 1 0041799

(51) Int. Cl.
A61B 6/00      (2006.01)
A61B 5/00      (2006.01)

(52) U.S. Cl.
CPC ............ *A61B 5/445* (2013.01); *A61B 5/0075* (2013.01); *A61B 5/0077* (2013.01); *A61B 5/7246* (2013.01); *A61B 2562/0242* (2013.01)

(58) Field of Classification Search
CPC ..... A61B 5/445; A61B 5/0059; A61B 5/0073; A61B 5/0095
See application file for complete search history.

(56) References Cited

U.S. PATENT DOCUMENTS

2010/0056928 A1*   3/2010   Zuzak ................. A61B 5/0071
                                                           600/476

\* cited by examiner

Primary Examiner — Michael J D Abreu
(74) Attorney, Agent, or Firm — McDermott Will & Emery LLP

(57) ABSTRACT

A near-infrared spectrum imaging system for diagnosis of the depth and the area of burn skin necrosis comprises a spectrum imager and a computer controlled system. The spectrum imaging system comprises a light source (101), an optical lens (102), a filter (103), a driving controller (105a, 105b, 104), and a CCD camera (106). The filter (103) uses a wide-spectrum liquid crystal tunable filter (LCTF) or an acousto-optic tunable filter (AOTF) that obtain 1100-2500 nm waveband spectral signals of burn skin necrosis tissue of a target region. A compute controlled system is internally provided with a universal module, a data module, a spectrum correction module, a spectrum matching module, and a burn wound three-dimensional synthesizing module. The spectrum imager obtains spectral image data of burn skin necrosis tissue of a target region and inputs the data into the computer controlled system, and the computer controlled system performs image analysis and processing of the data; the depth and the area of burn of the target region can be (Continued)

obtained by means of spectral matching and recognition on a spectral reflectance curve corresponding to each image pixel in an spectral image and a standard spectral reflectance curve in a burn skin necrosis spectral database in a data module, and the data is synthesized into a three-dimensional image for display.

11 Claims, 8 Drawing Sheets

NEAR-INFRARED SPECTRUM IMAGING SYSTEM AND METHOD FOR DIAGNOSIS OF DEPTH AND AREA OF BURN SKIN NECROSIS

FIELD OF THE INVENTION

The present invention relates to the field of tissue injury and spectral imaging technology.

BACKGROUND OF THE INVENTION

Burns are common diseases in peacetime and wartime, especially in wartime. After burn, the mortality rate, appearance damage rate and mutilation rate are high, the treatment period is long, which directly threaten the life safety and the health of the body, which brings heavy burden to the society and the family.

At present, the accurate judgment of the degree of skin tissue damage caused by burns is still a major problem in burn surgery, but the most common method used in clinical diagnosis of burn depth still mainly relies on clinical experience, including the observation of the appearance of the burn wound, the condition of capillary refill, and the feeling of the wound on the touch and the pain of acupuncture, etc. Data shows that accuracy of the empirical diagnosis of wound surface by the world's best burn doctors is only about 70%, that is, at least 30% of the healthy tissue may be incorrectly cut or 30% of the necrotic tissue may be retained undesirably during the burn operation. The former can remove extremely valuable skin appendages and its related stem cells remaining on the wound and other normal tissues along with necrotic tissue, and this has an important influence on the speed and quality of wound healing. The latter can increase the depth of the burn, that is, wound may become deeper. In addition, deep burn skin tissue lesions can be deep into the muscle and even bone, which is far beyond the anatomical depth of the skin tissue, and the treatment and prognosis of this kind of injury are more complicated, therefore, the empirical diagnosis of burn depth only based on the naked eye identification has a limited guiding effect for the clinical treatment. Research data show that timely and accurate judgment and treatment can inhibit the speed and extent of the change of the burn wound surface from the superficial to the deep, and can effectively save the lives of patients, reduce complications, promote wound healing, accelerate the rehabilitation of patients.

The current "golden standard" for the burn diagnosis is still tissue pathological biopsy. There are several reasons why this cannot be applied to clinical practice: 1. the operation of a biopsy is traumatic to the body, which is not acceptable to some patients; 2. in a certain period of time, the pathological changes of the burned tissue are dynamic and continuous, therefore, it may not accurately predict the results by performing a single biopsy so as to preliminarily assess the damage degree in the early stage of the burn; 3. an experienced pathology expert is required, and this expert has to commit to this work for a long time. For the same reasons, skin collagen and immunohistochemical staining of vimentin technology that appeared subsequently also failed to be popularized in clinical testing.

Since the sixties of the 20th century, a variety of diagnostic techniques of burn depth have emerged in the field of burn wound diagnosis, such as fluorescence detection technique, near infrared thermal imaging technique, ultrasonic detection technique, laser Doppler technology, spectral Bio-technology and so on.

Fluorescence detection technique uses intravenous injection of fluorescent substance to evaluate the depth of the wound according to the fluorescence intensity, peak value and time phase characteristics, which are produced when the wound is irradiated with different excitation light. However, substances such as the wound ointment, antiseptics, dressing, and biological agents have a relatively great impact on the ICG detection results of the burn wound. In addition, the fluorescence is weak when the deep burn blood vessel is damaged or is blocked, which increase detection error.

Infrared thermal imaging technique evaluates burn depth of the wound by detecting the thermal radiation of different burn skin. Lawson et al. firstly use this technique to detect the depth of the wound. However, this method has higher requirements for the detection condition, and needs constant ambient temperature and equilibrium time, both evaporation and cooling of wounds greatly affect the detection results. Due to high equipment cost, large individual difference, high false positive and many other factors, Deep II and III degree wounds cannot be well distinguished, limiting its wide application in clinical.

Kalus evaluated burn depth by first using B ultrasound scan, the main principle of which is to observe the boundary of living tissue and necrotic tissue, and then diagnoses based on the echo patterns of normal skin and different burn tissues. The main factor that limits its clinical application is that contact of the wound during the operation is required. In addition, practice has proved that the diagnostic accuracy is low, and is not superior to the subjective empirical diagnosis.

Laser Doppler technique products are currently the only device approved by the United States FDA to be used for the diagnosis of burn wound depth. Its principle is to use the Doppler shift to detect blood cell flow in the micro blood vessels of the wound tissues. The blood flow of superficial burn wound is relatively rapid, and that of the deep burn wounds is slow, so the superficial and deep burns can be distinguished based on this.

Early spectral technique evaluates the depth of burn using different attenuation of different spectra after absorption by blood in the wound. Anselmo et al. first proposed this technique and used it in clinical diagnosis. Three kinds of spectra green, red and blue were used to diagnose the wound, and the accuracy rate of diagnosis is as high as 79%. Based on this technique, an instrument designed by Heimbach et. al. used in clinic has 80% diagnostic accuracy of the wound that was not healed in three weeks. In recent years, the method based on spectral technique to diagnose burn depth has been further developed and gradually extended to the field of near infrared spectroscopy. In 2001, Sowa et al. developed a new method to judge the depth of burn using differences of oxygenated hemoglobin, deoxygenated hemoglobin and tissue moisture in the blood when the skin is burned shown in the absorption spectra of near infrared light in a wavelength range of 700-1000 nm, and measuring the total hemoglobin in the blood (tHb), tissue oxygen saturation ($StO_2$) and water ($H_2O$) content, and carried out the experimental study on the animal model of 3 h after injury. In 2005, Milner et al. evaluated the degree of burn by orthogonal polarization spectral (OPS) of wavelength 548 nm (hemoglobin absorption wavelength) for the first time. In 2009, Cross et al. studied the relationship between the degree of edema of skin tissue and the burn depth after burn in the wavelength range of 500-1000 nm. However, the core principles of the above research are to judge the depth of burn indirectly based on the changes of oxygen carrying status of red blood cell in blood, and tissue water content changes of the skin before and after skin burn (see FIG. 9), and precise information about the depth and area of burn skin tissue necrosis cannot be provided directly.

At present, spectral imaging technique has matured, and is used in the field of space remote sensing and mapping, agriculture, exploration and other fields of science and technology. This technique combines spectral analysis technology with image analysis technology, and meets the new concept of comprehensive qualitative, quantitative and positioning analysis, its visualization, non-contact and non-invasive and other excellent characteristics show its potential probability to be used as a new kind of high specificity and high accuracy burn wound diagnosis tool. At present, its imaging band is mainly in the visible and near infrared spectrum, but the spectral resolution is generally low, and the scanning precision is about 50 nm, which cannot meet the needs of medical fine research yet. Currently, the bands of imaging spectrometer for the study of burn medicine are mainly in 400-700 nm and 700-1100 nm, the basic principle of the spectral biology is still mainly analyzing the changes of oxygen carrying status of red blood cells in the blood and tissue water content of the skin. Among them, a typical patent literature is "visible-near infrared spectroscopy technology in burn injury assessment" (U.S. Pat. No. 860,554 B2), which mainly studied changes of oxygenated hemoglobin, deoxyhemoglobin, and water content of the blood of the skin before and after burn in 500-1100 nm band, and the depth of burn is indirectly suggested; therefore, accurate information about skin tissue necrosis cannot be provided.

The existing spectral imaging techniques can not accurately distinguish the skin necrosis tissue and acquire the spectral images of the skin tissue tomography, there is also a key point that the spectral resolution and imaging spectral range thereof cannot distinguish skin necrotic tissue and acquire the tomography images thereof, that is, a high resolution narrow band and wide band tunable filter is the core problem.

Therefore, so far, there is no such diagnostic equipment and related methods which can directly and accurately distinguish the depth of the necrotic tissue, accurately identify the boundaries of the necrotic tissue and normal tissue.

SUMMARY OF THE INVENTION

The present invention is made with respect to the above defects existing in the prior art and aims to provide a near infrared spectrum imaging system and method for the diagnosis of burn skin necrosis depth and area, which uses super spectrum imaging instrument with high resolution, wide field of view angle, and high efficiency to obtain the key information of degeneration and necrosis tissue of burn skin by non-contact and noninvasive method and is visible. It obtained the accurate information of burn skin necrosis area and depth by information processing; and providing key information about the necrotic tissue of skin burn to clinicians for clinical treatment and clinical surgery.

The technical solution adopted by the present invention is as follows:

A near-infrared spectrum imaging system for diagnosis of the depth and the area of burn skin necrosis comprising a spectrum imager and a computer controlled system.

Wherein the spectrum imager comprises a light source, an optical lens, a wide-spectrum liquid crystal tunable filter (LCTF) or an acousto-optic tunable filter (AOTF) that obtain spectral signals of 1100-2500 nm waveband, a driving controller, and a CCD camera;

the computer controlled system is internally provided with a universal module, a data module, a spectrum correction module, a spectrum matching module, and a burn wound three-dimensional synthesizing module.

The system obtains spectral image data of burn skin necrosis tissue of a target region by the spectrum imager, and inputs the data into the computer controlled system, and performing image analysis and processing, that is, firstly spectrum correction is performed by means of the spectrum correction module, and spectral matching and recognition is performed by means of the spectrum matching module on a spectral reflectance curve corresponding to each image pixel in an corrected spectral image and a standard spectral reflectance curve of a burn skin necrosis spectral database in a data module, the depth and the area of burn of the target region are obtained, and finally a three-dimensional image of the target region is synthesized by the burn wound three-dimensional synthesizing module and is displayed by a display device.

The standard spectral reflectance curve in a burn skin necrosis spectral database and burn depth in the pathology database have one to one matching relationship, features of the spectral reflectance curves of burn skin necrosis in 1100-2500 nm waveband are used to quantify necrotic signal of burn skin, and the necrotic signal and pathological data are correlated, so that standard spectral reflectance curve in a burn skin necrosis spectral database is matched with burn depth in pathological database, each standard spectral curve in the burn skin necrosis spectral database represents a burn depth.

The features of the spectral reflectance curves of burn skin necrosis in 1100-2500 nm waveband include shape of the spectral reflectance curve, average amplitude of the curve, and the amplitude difference between peaks and valleys in the curves.

The necrotic signal in the skin is, after the skin burns and necrosis, the change of the spectral information which is caused by the breakage of the chemical bonds of the original protein, nucleic acid and high molecular weight hydrocarbons and other biological macromolecules in the skin when experiencing heating damages, the chemical bonds mainly include C—N, N—H and O—H bond, and also include unsaturated conjugate bond: C=C, N=N, N=O. Such changes of the spectral information are the necrotic signal.

Liquid crystal tunable filter (LCTF) used in this system is critical. Liquid crystal tunable filter (LCTF) includes a liquid crystal tunable filter and a drive controller (FIG. 3).

The liquid crystal tunable filter is a multistage cascaded structure, and includes: a set of electronically controlled liquid crystal wave plates, a set of fixed phase retarders and a set of polarizers. The polarizers, the electronically controlled liquid crystal wave plates and the fixed phase retarders are arranged in parallel with each other in sequence, formed as a stack in sequence to form multistage, but a fixed phase retarder can be optionally set in the first stage (FIG. 4).

The transmitted polarized light directions of all the polarizers are parallel to each other, fast axis directions of all electronically controlled liquid crystal wave plates and transmitted polarized light directions of all the polarizers are at an angle of 45°.

The electronically controlled liquid crystal wave plate in each stage of the structure is controlled by drive controller which loads driving signal (FIG. 5).

Especially, the electronically controlled liquid crystal wave plate includes an intermediate nematic phase liquid crystal layer as well as an alignment film, a transparent conductive film, and a transparent substrate which are sequentially and symmetrically arranged on both sides, the alignment films on both sides of the nematic phase liquid crystal layer are antiparallel in the directions of friction, the liquid crystal molecules in the liquid crystal layer are arranged along the surface, the thickness of the liquid crystal layer is controlled by setting the transparent spacer in the liquid crystal layer (FIG. 6).

The liquid crystal tunable filter can use the drive control mode of conventional LCTF, but this will lead to a slower rate of spectral scanning, and the response time may reach several hundred milliseconds, and for dynamic spectrum imaging, this restricts the time for obtaining the spectral information of the spectral imaging system to a great extent, and causes great difficulty to the clinical image acquisition and subsequent image processing. Therefore, to improve the image processing speed of the instrument and to better achieve the high efficiency of the invention, the invention adopts an overvoltage driving mode, that is, the driving controller loads AC overvoltage driving signals of different amplitudes on the electronically controlled liquid crystal wave plate, an overvoltage driver is used for driving: if a liquid crystal wave plate requires a driving voltage $V_2$, firstly a narrow pulse with a short duration t is applied when driving, the value range of t is between 0-50 ms, t is not equal to zero, the voltage magnitude of $V_3>V_2$, the amplitude range of $V_3$ is between 10-50V, and then applying $V_2$ driving voltage, the voltage amplitude is between 0-10V but not equal to 0, alternating frequency is in 0.5-5 KHz (FIG. 7).

Therefore, the above system can be used to diagnose the boundary between normal skin tissue and burn skin necrosis tissue and the depth of burn skin necrosis, and flowing steps are included (FIG. 8):

(1) illuminating the target region of the burn skin by the light source;

(2) collecting the spectral images of the target region in 1100-2500 nm waveband by LCTF or AOTF and CCD cameras, obtaining the spectral data and image data of burn skin necrosis, and inputting into the computer control system;

(3) performing image analysis and processing by the computer controlled system:

(3.1) spectrum correction: the amplitude of spectrum curve corresponding to each image pixel of the spectral image in the original spectral image of the target region is divided by the amplitude of spectral curve corresponding to the image pixel of the spectral image of the white board in the same condition so as to remove the influence of the background light and the heterogeneity of the light source, and the spectral reflectance curve of the target region is obtained;

(3.2) spectral matching and identifying: performing comparative analysis of spectral reflectance curve of each image pixel in the spectral image of the target region after the correction with the standard spectral reflectance curve of the burn skin necrotic spectral database, that is, matching and identifying the skin reflectance spectra curve of known burn depth with spectral reflectance curve of target region, and calculating the similarity value between the spectral reflectance curve of the image pixel in the target region and the standard spectral reflectance of different burn depth skin, the burn depth corresponding to the maximum similarity value is taken as the burn depth of the target region image pixel, then each image pixel in the target region is identified by matching, and the burn depth and area of the target region are obtained;

(3.3) spectral image synthesis and display: three dimensional syntheses and display of the data of burn depth and burn area of the target region.

The imaging system and method provided by the present invention as above have the characteristics of high resolution, wide field of view angle and high efficiency, and is capable of indicating the changes of the spatial structure of the skin caused by the degeneration of tissue protein before and after the skin burn. Therefore, the micron level information about the boundary between normal skin tissue and necrotic tissue and the depth of burn skin necrosis are provided in a non-contact and noninvasive manner and the visualization is achieved. Finally, the key information of necrosis depth and area of the skin burn and necrosis tissue in micron level was provided to clinicians, which can be beneficial to guide clinical therapy and clinical surgery and to avoid cross infection and patient pain caused by medical detection to the maximum extent. It is beneficial for clinical diagnosis, treatment and prognosis.

Herein the burn covers thermal burns, scald, chemical burns, electrical shock injury, radiation injury, frostbite etc.

EMBODIMENTS

In order to better illustrate and explain the technique of the present invention and its effects, the present invention is described in further detail below with reference to the drawings and research experiment process of the present invention.

Figure 1:
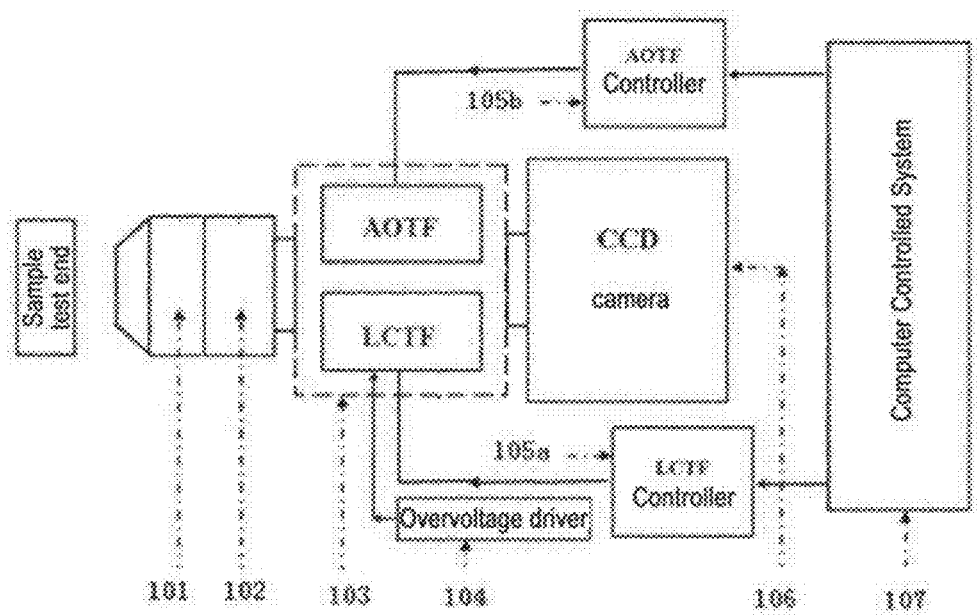
FIG. 1 is a schematic diagram of the structure of the diagnostic system of the present invention.

I. The Clinical Diagnosis System for the Depth and the Area of Burn Skin Necrosis The diagnosis system mainly includes the spectral imaging instrument and the computer control system. The structure is shown in FIG. 1, wherein:

1. The spectral imager: consisting of an illumination light source 101, an optical lens 102, a filter 103 (using a liquid crystal tunable filter LCTF and an acousto-optic tunable filter AOTF), a CCD camera 106, a LCTF controller 105a and AOTF controller 105b and an overvoltage driver 104. They are assembled in the form of a conventional spectral imager. The performance parameters of each component can be selected as follows:

Liquid crystal tunable filter (LCTF): working band: 900 nm~2500 nm; spectral resolution: 5-20 nm; optical transmittance: 5-30%; field of view angle: 1-10°.

CCD camera: types: Daheng DH-SV1411GX; resolution: 1394×1040 pixels; frame rate: 15 frames/sec; data interface: gigabit network port.

Illumination light source: halogen lamp light source: OCEANS United States; spectral range: 400 nm~2500 nm; light source illuminating manner: ring lighting.

Optical lens: types: Optistar; focal length: 50 mm (fixed focus lens), clear aperture: 55 mm.

Figure 7:
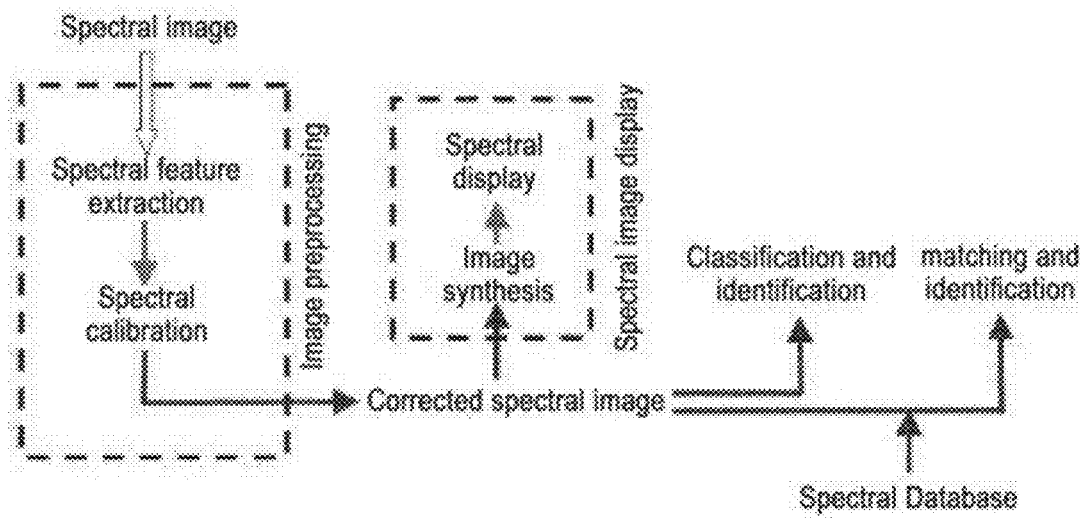
FIG. 7 is a processing flow chart for image analysis and processing.
Figure 8:
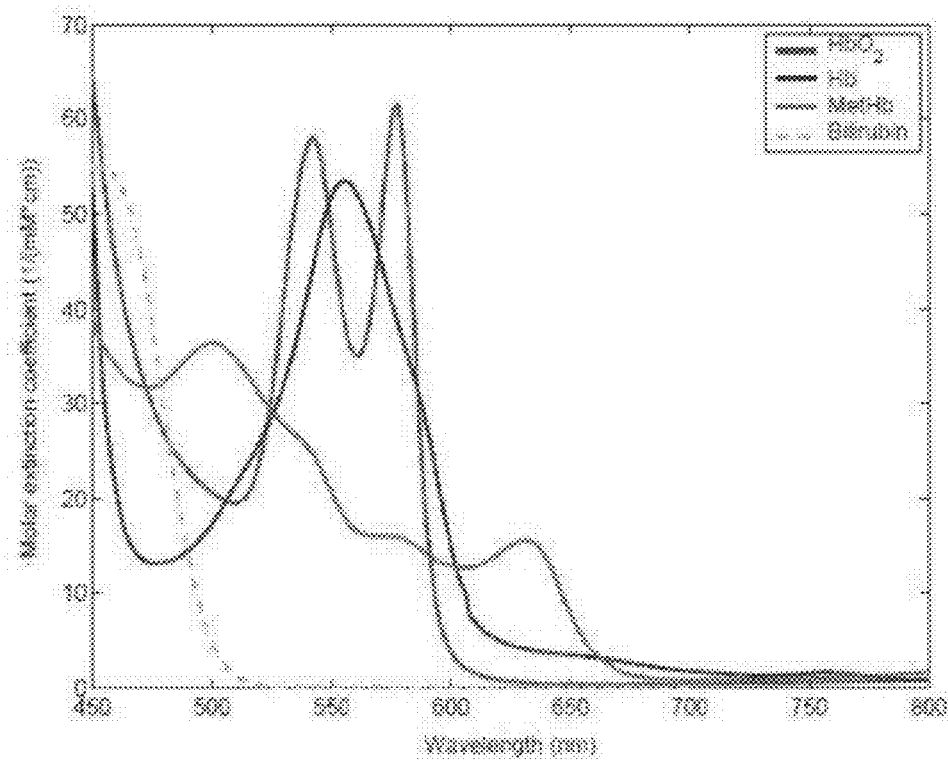
FIG. 8 shows the absorption spectra of water, hemoglobin and deoxyhemoglobin.

LCTF over-voltage drive controller: t in the range between 0-50 ms, the voltage magnitude $V_3 > V_2$, the amplitude range of $V_3$ is between 10-50V, and then driving voltage of $V_2$ is applied, the voltage amplitude is between 0-10V, alternating frequency is in 0.5-5 KHz (FIG. 7).

The main parameters of such spectral imager are: working band: 900 nm~2500 nm; spectral resolution: 5-20 nm; spatial resolution: 10-200 μm, optical transmittance: 5-30%; field of view angle: 1-10°.

Figure 2:
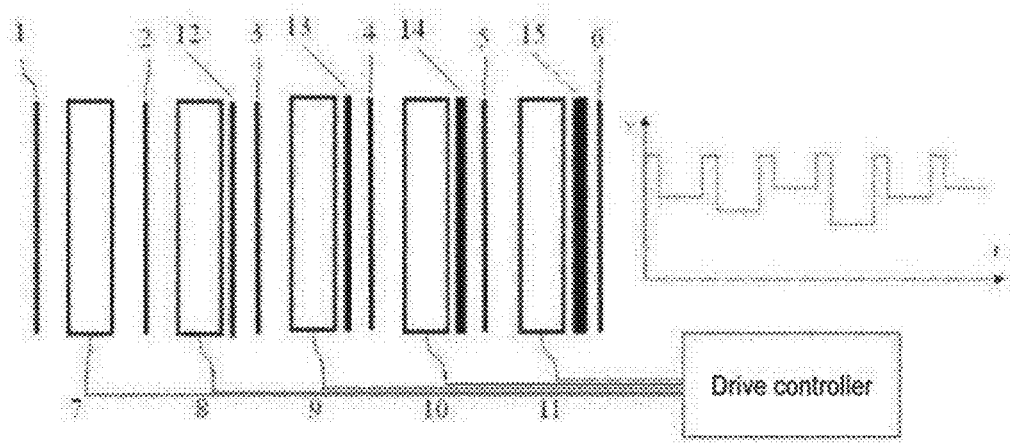
FIG. 2 is the structure of the liquid crystal tunable filter.
Figure 4:
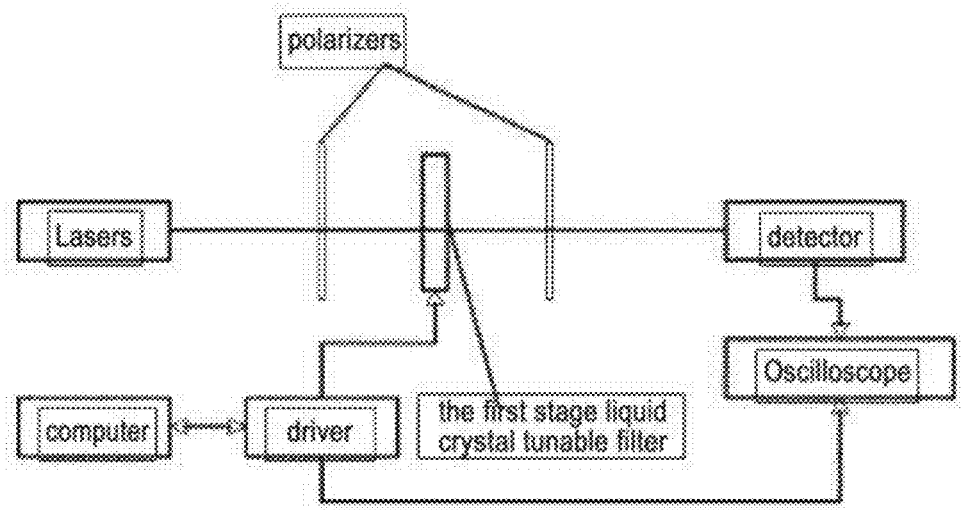
FIG. 4 is a schematic diagram of the optical path for measuring the liquid crystal wave plate response time.

The structure and driving of the liquid crystal tunable filter (LCTF) adopted by the present invention are shown in FIG. 2:

See FIG. 2, it uses five cascade structures of liquid crystal tunable filter, which comprises the polarizers (1, 2, 3, 4, 5, 6), electronically controlled liquid crystal wave plates (7, 8, 9, 10, 11) and fixed phase retarders (12, 13, 14, 15) (a total of five stages, the first stage was not set with a fixed phase retarder). Directions of the transmitted polarized light by the polarizers (1, 2, 3, 4, 5, 6) are parallel to each other, fast axis directions of electronically controlled liquid crystal wave plates (7, 8, 9, 10, 11) and transmitted polarized light directions of the polarizers (1, 2, 3, 4, 5, 6) are at an angle of 45°, the polarizers (1, 2, 3, 4, 5, 6) and the electronically controlled liquid crystal wave plates (7, 8, 9, 10, 11) and the fixed phase retarders (12, 13, 14, 15) are arranged in parallel with each other and interval stacked. The liquid crystal wave plate in each stage of the structure is controlled by a drive controller. The right side of FIG. 4 is the schematic diagram of the voltage drive signal loaded on the electronically controlled liquid crystal wave plate in each stage of the liquid crystal tunable filter, the signal is an AC overvoltage driving signal, the voltage amplitude is between 0-20V, alternating frequency is in the 0.5-5 KHz. The driving mode is: if a liquid crystal wave plate requires a driving voltage $V_2$, firstly a narrow pulse is applied when driving, the magnitude of $V_3 > V_2$, and then applying driving voltage $V_2$. Under the control of the drive controller, the liquid crystal wave plate of each stage is loaded with AC overvoltage driving signals of different amplitudes to achieve the fast spectral scanning of liquid crystal tunable filter.

Figure 3:
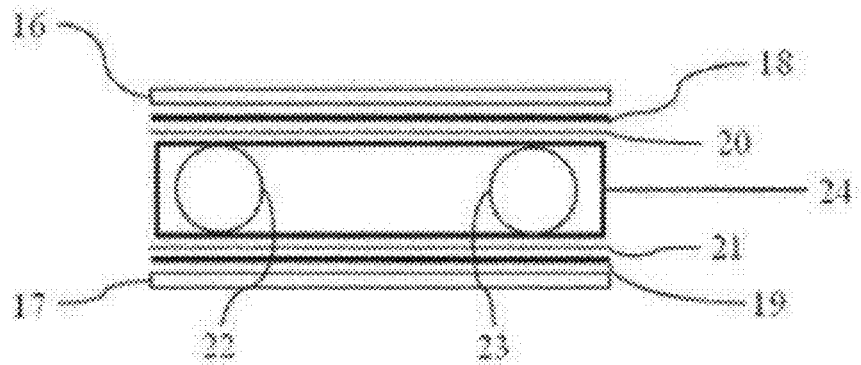
FIG. 3 is the structure of liquid crystal wave plate.

FIG. 3 is a schematic diagram showing the structures of the electronically controlled liquid crystal wave plates (7, 8, 9, 10, 11), including the glass substrates (16, 17), ITO transparent conductive films (18, 19), PI alignment films (20, 21), thickness control transparent spacers (22, 23) and liquid crystal layer 24. ITO transparent conductive films (18, 19) are connected to the drive controller (i.e., multichannel driving source) through the electrodes to provide electric field for the liquid crystal layer 24, which makes the orientation of the liquid crystal molecules rotate, and changes the phase delay of the electronically controlled liquid crystal wave plates (7, 8, 9, 10, 11), so as to control the polarization state of the incident light. The PI oriented films (20, 21) are coated on the inner surface of the glass substrates (16, 17), after baking, friction and other processes, the liquid crystal molecules in the liquid crystal layer 24 can be induced to be arranged in a specific direction and the electronically controlled liquid crystal wave plates are made to have the birefringent optical characteristics of crystal; the liquid crystal layer 24 is formed by perfusing nematic liquid crystal materials between the glass substrates. The thickness of the liquid crystal layer 24 is controlled by the thickness controlling spacers (22, 23), and the refractive index difference of Δn is between 0.05~0.30. The thickness controlling spacers (22, 23) can be made of glass fiber, glass beads, plastic beads or photospacer, etc.

In order to prove the effectiveness of the overvoltage driving mode, the overvoltage driving signal is loaded on a single-stage liquid crystal wave plate and the response time thereof is measured. The light path for time response characteristic measurement is shown in FIG. 4, the liquid crystal wave plate is provided with over-voltage drive signal by the driving controller and is placed between two parallel polarizers, the wavelength of the laser is 632.8 nm, the photoelectric detector uses the visible light sensitive device having a photoelectric response speed of sub-micro level, the photoelectric signal of the detector is transmitted into the oscilloscope for recording.

Figure 5A:
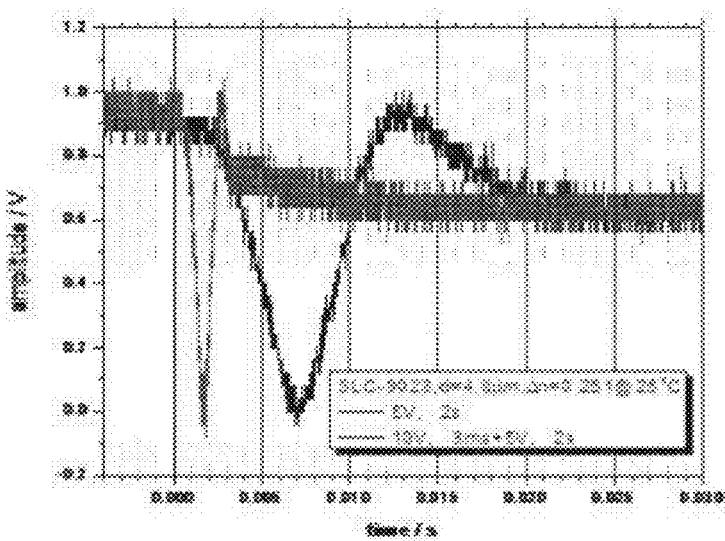
FIG. 5*a* is the photoelectric response measurement results of liquid crystal wave plate, having a thickness of 4.8 mm and perfused with liquid crystal material SLC-9023, driven by overvoltage.
Figure 5B:
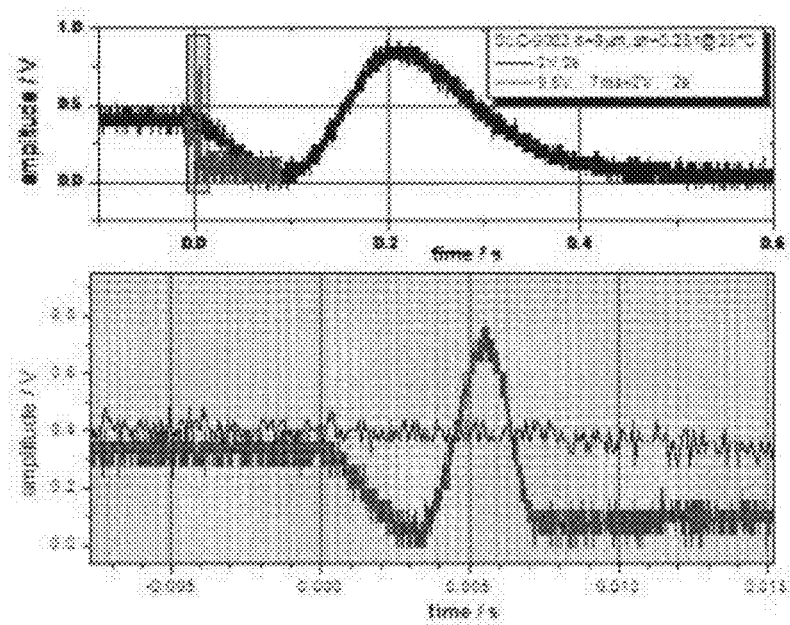
FIG. 5*b* is the photoelectric response measurement results of liquid crystal wave plate, having a thickness of 8.0 mm and perfused with liquid crystal material SLC-9023, driven by overvoltage.
Figure 6:
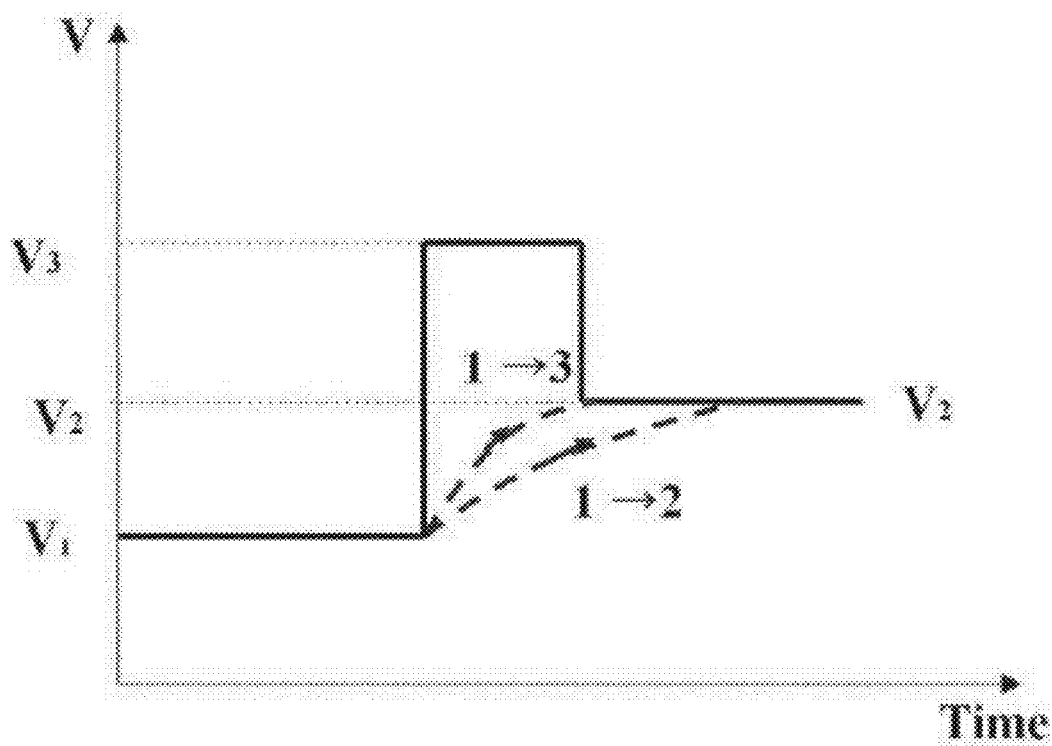
FIG. 6 is a schematic diagram of the driving mode for an over voltage driver.

FIGS. 5a and 5b are the photoelectric response measurement results of liquid crystal wave plates, having a thickness of 4.8 mm and 8.0 mm respectively and perfused with SLC-9023 liquid crystal material, driven by overvoltage. From FIG. 5a, it shows that the time to reach the steady state for the liquid crystal wave plate having a thickness of 4.8 mm is 25 ms under a conventional 5V voltage driving, and the time to reach the steady state is only 3~5 ms (voltage between 10-50V is appropriate) under a 10V, 3 ms overvoltage; similarly, it can be seen from FIG. 5b that the time to reach the steady state is 450 ms for a liquid crystal wave plate having a thickness of 8.0 mm under a conventional 2V driving voltage, and the time to reach the steady state is only 7 ms under a 9.6V, 7 ms impact driving. The experimental results show that the overvoltage driving method can improve the photoelectric response time of the liquid crystal wave plate effectively, so as to realize the rapid spectral scanning and imaging of the liquid crystal tunable filter.

The system can also be switched automatically by using an acoustic optic tunable filter (AOTF) and a liquid crystal tunable filter (LCTF). Acousto-optic tunable filter (AOTF) is an acoustic optic modulation device, which is composed of a uniaxial birefringent crystal (usually TeO2), piezoelectric transducer bonded to one side of a uniaxial crystal, and a high frequency signal source for piezoelectric transducer.

The spectral scanning speed of AOTF is very fast and is suitable for scanning the instantaneous state of an object. In recent years, AOTF has been widely used in many aspects, such as image processing, monitoring, collection of color information, electro optic signal scanning generator of spectral analysis and so on. The working principle of AOTF is to use the Prague diffraction effect of sound waves on light that is incident to the propagation medium during its propagation in anisotropic media. When inputting the radio frequency signals of certain frequency, AOTF diffracts the incident multicolor light so that monochromatic light of the wavelength λ is picked out. The wavelength λ of the monochromatic light and the rf frequency f have a one to one relationship. That is, a required wavelength of light can be selected quickly by the tuning of the electrical signal. The selected light wave enters the image acquisition system through a CCD detector, and the spectral image is stored in the computer by the image acquisition software. After a series of algorithms and database comparison, an ideal image can be displayed on the computer.

2. The computer controlled system, which is internally provided with a universal module, a data module, a spectrum correction module, a spectrum matching module, and a burn wound three-dimensional synthesizing module; the image analysis process is shown in FIG. 7.

The universal module controls the on and off of the light source, power rationing for each part of the hardware in the spectral imager, as well as various ports and interfaces of the system;

The data module includes the burn skin necrosis spectral database and burn skin necrosis pathology database; the wave band of the spectral reflectance curve in the burn skin necrosis spectral database is 1100-2500 nm, sources of the spectral reflectance curve data include fiber spectrometer and medical imaging spectrometer; the spectral reflectance curve in the burn skin necrosis spectral database and the burn depth in the burn skin necrosis pathology database have a one to one matching relationship, that is, the spectral reflectance curve can be used to represent the depth of burn. Specifically, features of the spectral reflectance curves of burn skin necrosis in 1100-2500 nm waveband are used to quantify necrotic signal of burn skin, and the necrotic signal and pathological data are correlated so that standard spectral reflectance curve in a burn skin necrosis spectral database is matched with burn depth in pathological database, each standard spectral curve in the burn skin necrosis spectral database represents a burn depth. The above features of the spectral reflectance curves of burn skin necrosis in 1100-2500 nm waveband include shape of the spectral reflectance curve, average amplitude of the curve, and the amplitude difference between peaks and valleys in the curves.

The spectrum correction module, wherein the amplitude of spectrum curve corresponding to each image pixel of the spectral image in the original spectral image of the target region is divided by the amplitude of spectral curve corresponding to image pixel of the spectral image of the white board in the same condition so as to remove the influence of the background light and the heterogeneity of the light source, and the spectral reflectance curve of the target region is obtained.

The spectral matching module, which is used for comparative analysis of spectral reflectance curve of each image pixel in the spectral image of the target region after correction with the standard spectral reflectance curve of the burn and necrotic skin spectral database, that is, matching and identifying the reflectance spectra curve for skin of known burn depth with spectral reflectance curve of target region, and calculating the similarity value between the spectral reflectance curve of the pixel in the target region and the standard spectral reflectance of different burn depth skin, the burn depth corresponding to the maximum similarity value is taken as the burn depth of the target region image pixel, then each image pixel in the target region is identified by matching, and the burn depth and area of the target region are obtained.

The three dimensional synthesis module of burn wound is used for three dimensional synthesizing and displaying of the data of burn depth and burn area of the target region.

II. The research process of the system and method of the present invention as well as the formation of burn skin necrosis spectral database and burns skin necrosis pathology database are described below.

(i) Experiment

1. Experimental Materials and Animals, Cells

Human cadaver skin, obtained from special leathers of Burns Institute of Southwest Hospital SD rats were purchased from the experimental center of Third Military Medical University Bama miniature pigs were purchased from the experimental animal center of Third Military Medical University Human skin fibroblasts, derived from skin discarded materials in primary culture of surgery 2. Instrument $CO_2$ Thermostat incubator: RKJ Japan XSJ-D inverted microscope: Chongqing optical instrument factory Super clean working table: Suzhou purification Equipment Company LAB cell culture box: USA Olympus inverted microscope: Japan TCL1200 Low temperature ultracentrifuge: Japan YLS-5Q Scald thermostatic instrument: Shandong Xinhua medical equipment company Medical visible hyperspectral imager: China Engineering Physics Research institute CP225D electronic balance: German Sartorius Company HH•W21•Cu600 Electric heating thermostatic water tank: Shanghai medical equipment Factory No, 7

LS-B50L Vertical pressure steam sterilizer: Shanghai Huaxian Medical instrument Co., Ltd.

LDR0.08-0.7G electric vacuum sterilizer: Shandong Xinhua. Medical Instrument Co., Ltd.

−80 □ low temperature refrigerator (HARRIS): HARRIS company, United States

Milli-Q Biocel pure water instrument: Milipore Company, USA

Various transferpettors: Eppendorf Company, USA

3. Reagent

DMEM culture medium: Gibco, USA

RPMI 1640 culture medium: Gibco, USA

Fetal bovine serum: Hyclone, USA

Calf serum: Institute of Hematology, Chinese Academy of Medical Sciences

Trypsin: Hyclone, USA

PI: Sigma, USA

CFSE: Japan Tongren Research Institute of Chemistry

Collagenase IV: Sigma, USA

TRIzol: Invitrogen USA

Trypan blue: Wuhan Boster Biological Technology, Co., Ltd.

Vimentin: Wuhan Boster Biological Technology, Co., Ltd.

4% paraformaldehyde: Beijing Zhongshan biological company

10% formaldehyde: Reagent Center of Third Military Medical University

Anti-off section: Beijing ZhongshanJinqiao biological company

4. The Solution and Preparation Thereof 3.1 DMEM Culture Medium:

$NaHCO_3$ 3 g, HEPES 4 g, glutamine 2 g, penicillin 100,000 U, streptomycin 100,000 U was added to every 1000 ml DMEM culture medium, pH 7.2, 0.22 μm membrane was used for filtering and sterilizing, stored at 4° C., 10% FBS was added before use.

3.2 0.25% Trypsin Solution:

Adding 0.25 g trypsin to 100 ml PBS (m/V) and stored at −20° C. for use.

3.3 PBS Solution:

40.2 g $Na_2HPO$, 40.2 g $NaH_2PO$, 0.02 g KCl, 0.8 g NaCl, $ddH_2O$ the volume was set to be 1.000 ml, PH 7.2, high pressure sterilization, and stored at 4° C.

(ii) Experimental Method

1. Calibration of Spectral Data Acquisition Conditions.

The near infrared fiber spectrum detector of the invention is subject to internal calibration, determining the optimum distance, angle and working time of the in vivo bioassays spectrum detection in combination with the actual measurement environment, and eliminating the adverse effects of background factors.

1.1 Calibrating the near infrared fiber spectrum detector using standard white board, continuously working for 10 min, 30 min, 60 min, 2 h, 4 h, and calibrating light intensity again, the mean was stable.

1.2 Taking into account the feature that the scattering of incident light due to the heterogeneity of the sample surface caused the decrease of the light intensity, the actual detection distance should not be too far away from the sample, otherwise the system error will be too large. This experiment used a measuring distance of 1-50 cm between fiber probe and the sample.

1.3 Considering that different detection angles had influences on the light intensity detected by near infrared fiber spectrum detector, the data collection was conducted with a vertical angle of the detector and the sample surface.

(iii) In vitro human skin burn model, rats skin burns model and Bama miniature pig skin burn animal model were established, and real-time in vivo spectral biological assay detection was achieved by using near infrared fiber spectrum detector.

1. Establishment of In Vitro Model of Human Skin Burns 1.1 Acquisition and Processing of In Vitro Human Skin 1) taking the in vitro human skin tissue of skin depot sources from liquid nitrogen; half a year of storage time, size was about 9×13 $cm^2$, average thickness was about 3 mm.

2) immersing into a sterile container including PBS at room temperature to restore the temperature; repeatedly eluting the impurities and foreign matter until it was clear without precipitation;

3) trimming the border with sterile scissors and removing the impurities;

4) washing with aseptic PBS for 3-5 times until the liquid was clear and no smell; covered with sterile wet gauze for use.

1.2 Establishment of the In Vitro Model of Human Skin Burns 1) taking human skin in vitro after trimming and cleaning and spreading to sterile sheet, with the epidermis side up;

2) wiping the moisture on surface of the skin by dry sterile gauze, ensuring that the surface of the skin in vitro is flat;

3) taking the thermostatic scald instrument and heating to 90 degrees, observing the effect of temperature stability for use;

4) YLS-5Q thermostatic scald instrument, probe size of 1.5×1.5 $cm^2$, which is heated to 92 degrees for use. Using 500 g gravity to put pressure on the surface of the skin in vitro to cause burns, burn time were 3 s, 5 s, 10 s, 15 s, 20 s, 30 s, 45 s, 60 s, 90 s, 120 s, 150 s, 180 s, respectively.

1.3 Preparation of the Thermal Burns Model of Human Skin In Vitro and Collection of Spectral Data 1) taking near infrared fiber spectrum detector, turning on the light source, debugging and testing software parameters, calibrating internally by the standard white board, removing noise and background curve, debugging instrument to a working state, running for ten minutes to observe stability of the working power and intensity of light source for use;

2) taking a standard whiteboard, adjusting the optimal distance of fiber probe to detect the sample standard whiteboard and fixing the position of the fiber probe, detecting by near infrared fiber spectrum detector and displaying the curve of standard white board, stand by after verification.

3) taking thermostatic heating probe, applying 500 g gravity onto the surface of the skin in vitro to cause burns, burn time were 3 s, 5 s, 10 s, 15 s, 20 s, 30 s, 45 s, 60 s, 90 s, and 120 s, respectively.

4) samples of the human burn skin in vitro and normal skin were taken for observing by near-infrared spectroscopy and the test results were recorded;

1.4 Collection and Fixing of the Pathology Sample of Model of Human Burn Skin In Vitro 1) cutting human skin strips in vitro of burn wounds of about 0.5×2.0 $cm^2$ by aseptic surgical instruments;

2) ensuring the specimens of skin in vitro trimmed and smooth, and putting them in 10% formaldehyde solution for fixing;

3) taking the fixed specimens of burn skin in vitro, conventional paraffin-embedded for use;

4) preparing slices with 6-8 microns thickness from the specimens on a slicer for use;

5) conventional dewaxing to water, HE staining;

6) observing under the microscope, taking pictures and recording.

Figure 9:
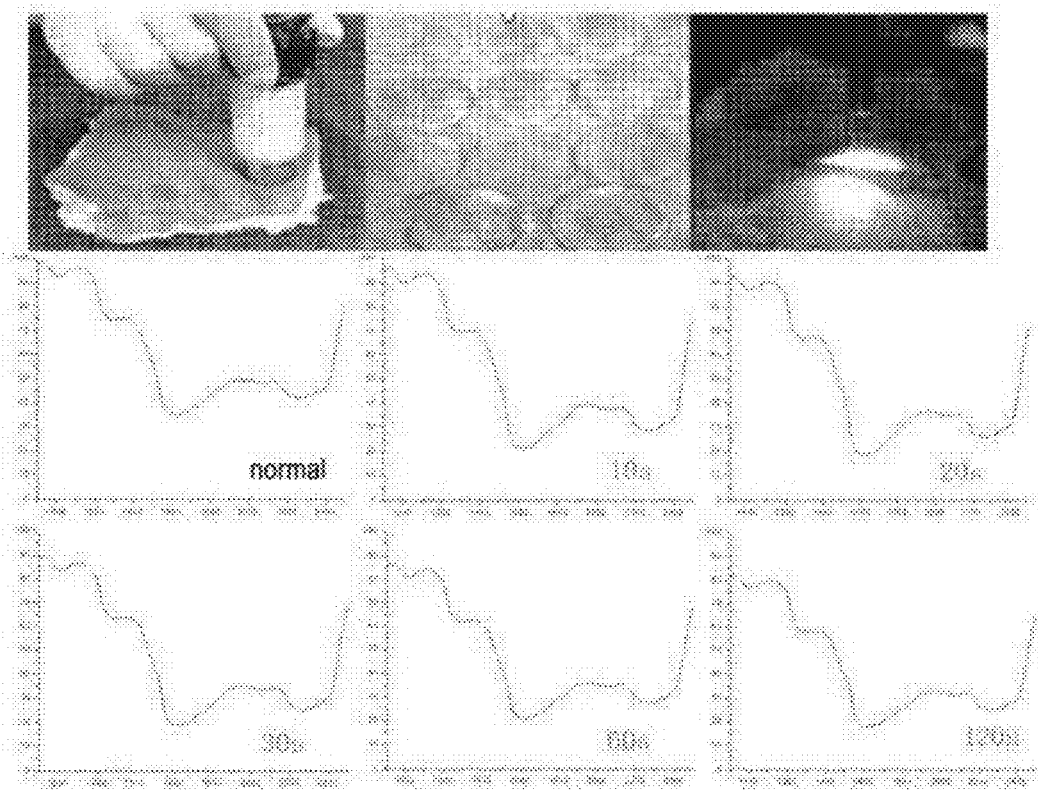
FIG. 9 is a spectrum detection diagram of the scald model for human skin in vitro.
Figure 10:
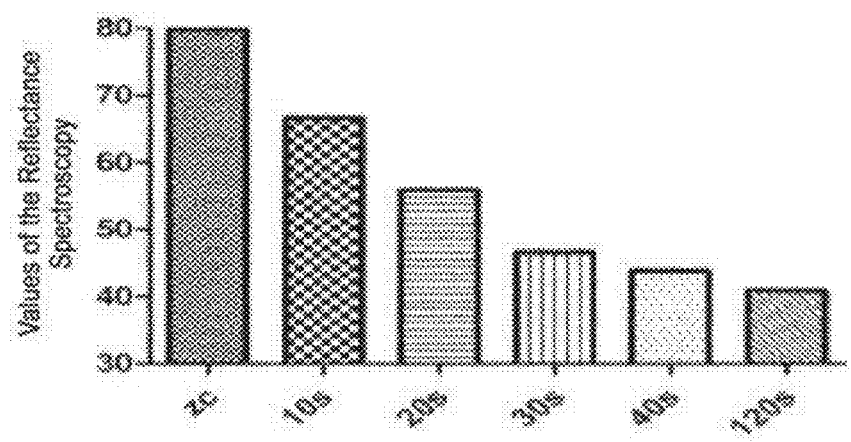
FIG. 10 is a summary histogram of results of the spectrum detection of scald model for human skin in vitro.

Spectrum detection results were shown in FIG. 9 and FIG. 10.

2. Establishments of the Model of Burn Skin of Rats 2.1 Preparation of the Model of Burn Skin of Rats 1) taking rats weighing about 300 g, male or female;

2) injecting 1% pentobarbital sodium (0.5 ml/100 g) into the abdominal cavity of the rats;

3) after anesthesia, soaking the back hair with liquid soap and removing them with a sterile blade to expose the back skin;

4) taking the thermostatic scald instrument and heating to 90 degrees, observing the effect of temperature stability for use;

5) taking 2.25 $cm^2$ thermostat hot head, applying 500 g gravity onto the back skin of rats in vitro to cause burns, burn time were 3 s, 5 s, 10 s, 15 s, 20 s, 30 s, 45 s, 60 s, 90 s, and 120 s, respectively.

2.2 Spectral Data Acquisition for the Model of Burn Skin in Rats 1) taking near infrared fiber spectrum detector, turning on the light source, debugging and testing software parameters, calibrating internally by the standard white board, removing noise and background curve, debugging instrument to a working state, running for ten minutes to observe stability of the working power and intensity of light source for use;

2) taking a standard whiteboard, adjusting the optimal distance of fiber probe to detect the sample standard whiteboard and fixing the position of the fiber probe, detecting by the near infrared fiber spectrum detector and displaying the curve of standard white board, stand by after verification.

3) placing the anesthetized burn rats in a fixed fiber probe to detect the burn wound and normal skin, respectively, and the distance was 1 cm, observing and recording the test results;

2.3 Collection and Fixing of Pathology Sample of Model of Burn Skin of Rats 1) cutting skin strips of burn wounds of rats about 0.5×2.0 $cm^2$ by aseptic surgical instruments;

2) ensuring the skin specimens in vitro trimmed and smooth, and putting them in 10% formaldehyde solution for fixing;

3) taking the fixed specimens of cut burn skin, conventional paraffin-embedded for use;

4) preparing slices with 6-8 microns thickness from the specimens on a slicer for use;

5) conventional dewaxing to water, HE staining;

6) observing under the microscope, taking pictures and recording.

Figure 11:
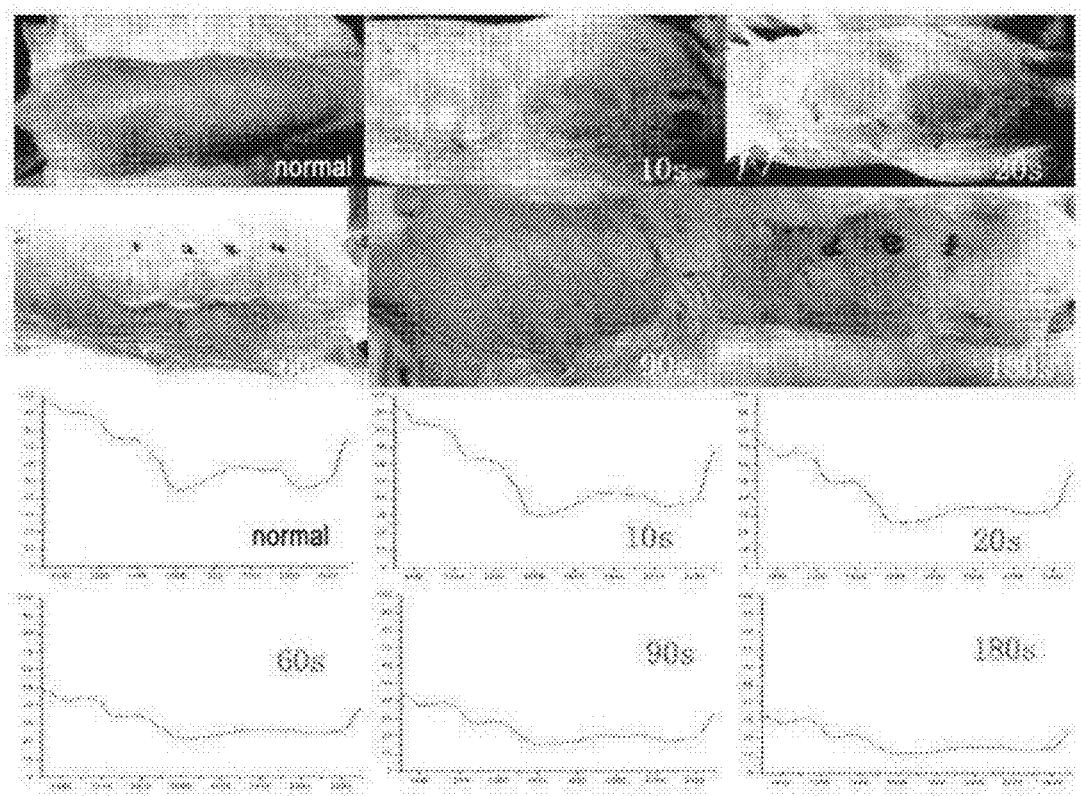
FIG. 11 is a diagram of spectrum detection of the scald model for rats.
Figure 12:
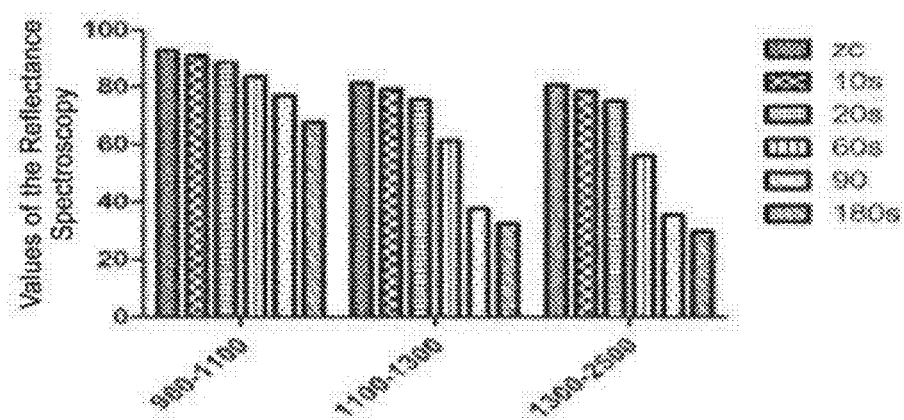
FIG. 12 is a summary histogram of results of the spectrum detection of scald model for rats.

Spectrum detection results were shown in FIG. 11 and FIG. 12.

3. Establishment of the Model of Gasoline Third-Degree Burns Skin of Adult Bama Miniature Pig and the Model of Thermostat Caused Two-Degree Burns Skin of Young Pigs 3.1 Preparation of the Model of Gasoline Third-Degree Burns Skin of Adult Pig 1) taking 2 years of adult Bama miniature pig, male or female;

2) injecting 4% pentobarbital sodium (0.5 ml/1 kg) into the abdominal cavity;

3) after anesthesia, soaking the back hair with liquid soap and removing them with a sterile blade;

4) take pure industrial gasoline evenly applied to the back of the skin, set aside;

5) igniting the gasoline by open flame to cause back gasoline burns, and the time was 30 s.

3.2 Preparation of the Model of Two-Degree Burns Skin of Young Bama Miniature Pig 1) taking 6 months of Bama miniature pig, male or female;

2) injecting 4% pentobarbital sodium (0.5 ml/1 kg) into the abdominal cavity;

3) after anesthesia, soaking the back hair with liquid soap and removing them with a sterile blade;

4) taking the thermostatic scald instrument and heating to 90 degrees, observing the effect of temperature stability for use;

5) taking 2.25 $cm^2$ thermostat hot head, applying 500 g gravity onto the back skin of rats to cause burns, burn time were 3 s, 5 s, 10 s, 15 s, 20 s, 30 s, 45 s, 60 s, 90 s, and 120 s, respectively.

3.3 Spectral Data Acquisition for the Model of Gasoline Burns Skin of Adult Pigs 1) taking near infrared fiber spectrum detector, turning on the light source, debugging and testing software parameters, calibrating internally by the standard white board, removing noise and background curve, debugging instrument to a working state, running for ten minutes to observe stability of the working power and intensity of light source for use;

2) taking a standard white board, adjusting the optimal distance of fiber probe to detect the sample standard white board and fixing position of the fiber probe, detecting by near infrared fiber spectrum detector and displaying the curve of standard white board, stand by after verification.

3) taking the anesthetized burn adult pig, adjusting position of fiber probe to detect the gasoline burn wound, two-degree burns and normal skin, respectively, and the distance was 1 cm, observing and recording the test results;

3.4 Collection and Fixing of Pathology Sample of the Model of Burn Back Skin of Bama Miniature Pig 1) cutting skin strips of burn wounds on back of adult pig for about 0.5×2.0 $cm^2$ by aseptic surgical instruments;

2) ensuring the skin specimens in vitro trimmed and smooth, and putting them in 10% formaldehyde solution for fixing;

3) taking the fixed specimens of skin, conventional paraffin-embedded for use;

4) preparing slices with 6-8 microns thickness from the specimens on a slicer for use;

5) conventional dewaxing to water, HE staining; observing under the microscope, taking pictures and recording.

Figure 13:
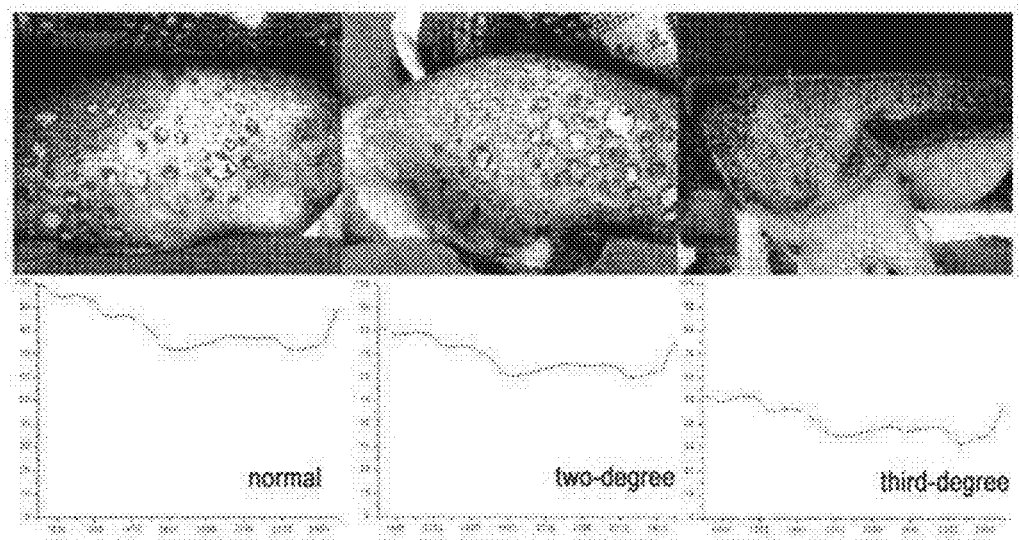
FIG. 13 is a diagram of spectrum detection of the scald model for adult pigs skin.
Figure 14:
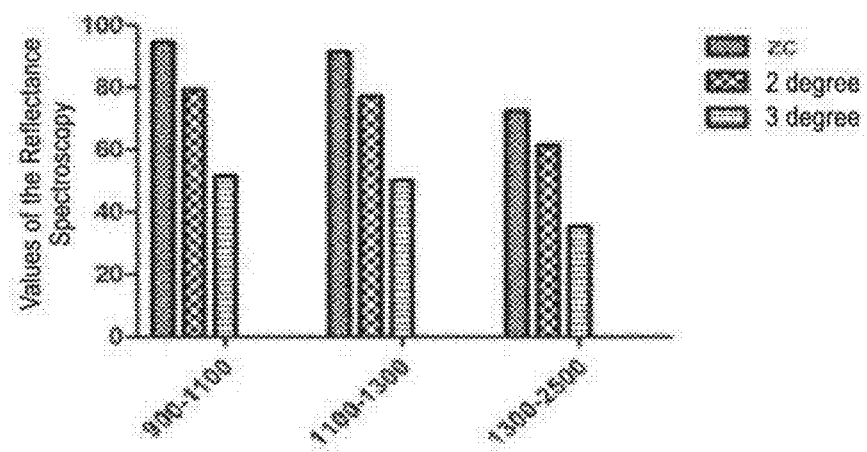
FIG. 14 is a summary diagram of the spectrum detection of the scald model for pig skin.

Spectrum detection results were shown in FIG. 13 and FIG. 14.

(iv) Spectral biological data of various burn models were analyzed, and the characteristic bands and characteristic amplitude as well as the inherent rules of the spectrum detection of the normal skin and the necrotic skin after burn were summarized.

1. The Analysis of Results of Spectrum Detection for Human Skin In Vitro after Burns 1) The reflection spectrum curve of the skin after burn changed in 1100 nm~2500 nm band, with the extension of burn time, the characteristic amplitude at a particular peak decreased;

2) the particular peak located in 1100-2100 nm.

2. The Analysis of Results of Spectrum Detection for Rat Skin after Burns

1) The reflection spectrum curve of the skin after burn changed in 1100-2100 nm band, with the extension of burn time, the characteristic amplitude at a particular peak decreased;

2) the particular peak located in 1100-2500 nm.

3. The Analysis of Results of Spectrum Detection for Skin of Bama Miniature Pig after Burns 1) The reflection spectrum curve of the skin after burn changed in 1100-2100 nm band, with the extension of burn time, the characteristic amplitude at a particular peak decreased;

2) the particular peak located in 1100-2500 nm.

4. Summary of Various Burn Model Test Results and Scientific Rule Thereof

1) Various burn models could be established and the actual requirements of spectrum detection were achieved to ensure the stability and reliability of the experimental data. At the same time, the experimental results obtained by detecting different burn models also showed some common characteristics.

2) The biological characteristic wave band of near infrared reflectance spectra of the skin after burn were 1100 nm~2500 nm.

3) The characteristics of the information changes were as follows: with the extension of burn time, the burn depth increased, and the characteristic amplitude of the characteristic wave band decreased.

(v) The pathological results of various burn models were analyzed and were comparatively analyzed with spectral biological data, so that inherent rules of the spectrum detection results of normal skin and skin necrosis after burn as well as pathological results of the depth of skin lesion were summarized.

1. The sample statistical analysis were carried out for spectral data of normal skin and burn skin lesions of various burn model, which were taken from the same site, the same depth and the same general condition, to establish the characteristic wave band and the stability of specific peak type, and to ensure high consistency of test results and data reliability.

2. The pathological resected specimens of the above wound collection site were routinely fixed, HE stained, taking pathology pictures under 200 times high magnification, and measuring the depth of skin damage by standard scale;

3. The results of wound spectral test were matched with the gold standard-results of HE pathological section depth measurement data; the stability of the matching results was detected, and system and human errors were excluded, and the matching results between spectral curve data of burns wounds and the traditional gold standard were obtained.

4. The data results of the real-time detection of the spectral detector for the fresh burn wound represented the skin burn depth detected by the corresponding gold standard, and the correlation matching was completed.

(vi) The spectral biological data of clinical cases of burns were detected and verified to summary inherent rules of spectral test results of normal skin and necrotic skin after burns as well as the results of skin pathology. Spectrum biological database of clinical burn patients having different depth of skin lesion was established. All of the collection of cases complied with the relevant requirements of the Ethics Committee of Southwest Hospital and with the consent of the patient.

1) The Wound Detection Standards and Data Acquisition Strategy were Established.

① The collection site: hyperspectral data of normal skin and various degrees of skin lesions of the patients was collected as much as possible;

② Collection conditions: quiet state, supine, the target site without any strong shaking and tremble during the acquisition; fiber probe perpendicular to the target region for collection, calibration 1 cm;

③ Inclusion criteria: exposed wounds in the extremities of young and middle-aged patients were preferred, extensive collection of various kinds of clinical cases;

④ Recording method: the basic information of patients+ real time photographs+spectral data collection+pathological diagnosis information;

⑤ Pathological specimen collection strategy: the specimen of collection site could be obtained by surgical removal, routine HE staining was performed, taking pathological pictures under 200 times high magnification, and measuring the depth of skin damage by standard scale.

2) Summary of the Results of Spectrum Detection of Normal Skin and Necrotic Skin after Burn.

① Spectral biological detection band which could effectively reflect the pathological changes after burn: 1100 nm~2500 nm.

② The reflection spectrum curve of the skin after burn changed in 1100-2500 nm band, with the extension of burn time, the characteristic amplitude at a particular peak decreased. The particular peak located in 1100 nm-2500 nm.

③ With the increase of the burn depth, in terms of the characteristic amplitude of the characteristic biological band, the biological rules indicated by the spectrum detection results of normal skin and necrotic skin after burn and the spectral biological rules summarized from the above spectral biological detection for model of burn skin in vitro, burn model of rats and Bama miniature pig are substantially the same.

④ Near infrared spectroscopy (1100-2500 nm) could be used for effective detection of the depth of skin lesion for the clinical burn patients.

3) Research and Analysis of the Matching Method of the Spectral Data of the Wound Surface and the Gold Standard ① Statistical analysis of large sample is carried out for the results of hyperspectral data collection for typical cases of burns from the same site, the same depth and the same general situation to establish the characteristic wave band and the stability of specific peak type, and to ensure high consistency of detection results and data reliability.

② Intraoperative pathological resected specimens of the wound collection site for the above cases were routinely fixed, HE stained, taking pathology pictures under 200 times high magnification, and measuring the depth of skin damage by standard scale.

③ Wound detection results were matched with the gold standard-detection data results of depth measurement of HE pathological section; the stability of the matching results was detected, system and human errors were excluded, and the matching results between spectral curve data of burns wounds and the traditional gold standard were obtained.

④ Spectrum detection databases of clinically normal skin and burn lesion were established, constantly expanding the data sample amount of the database to ensure that the results were stable and reliable, and developing the corresponding data analysis software to match the spectrum real-time monitoring results of spectrometer for the burn wound with database to reduce the error.

⑤ The results of real-time detection data of the spectrum detector for the fresh burn wound represented the skin burn depth detected by the corresponding gold standard, and the correlation matching was completed.

Figure 15:
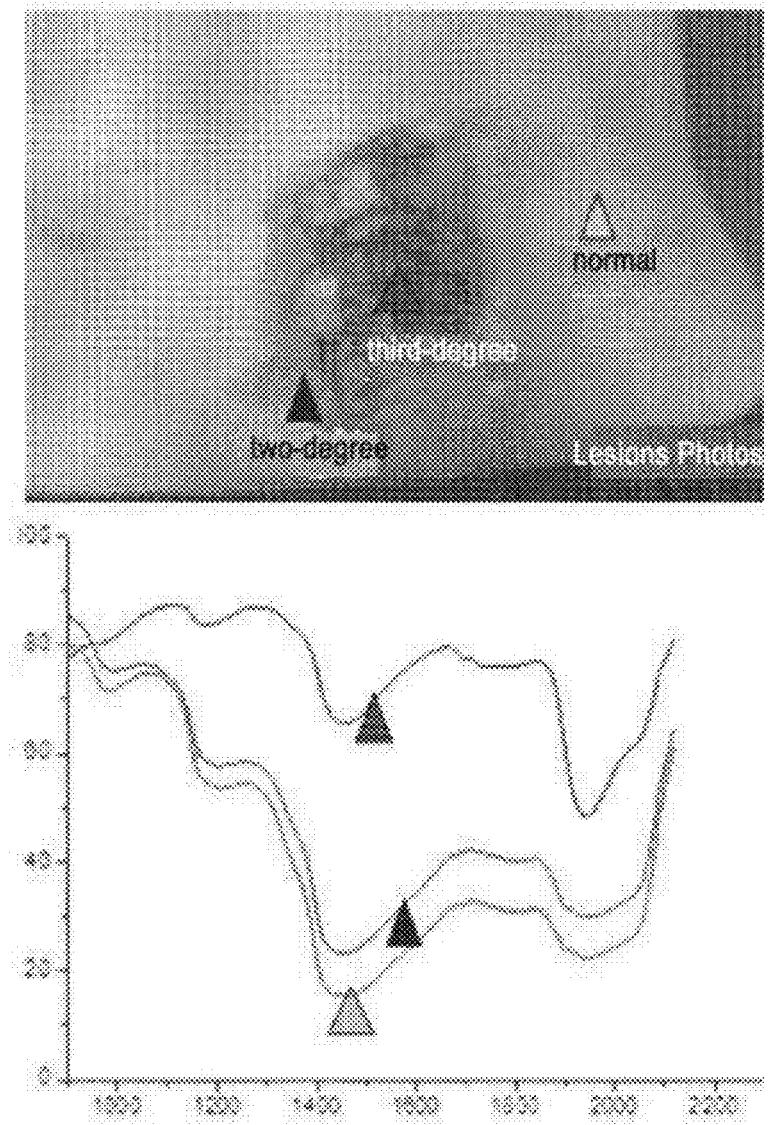
FIG. 15 is a diagram of the spectrum detection results for clinical burn patients.

4) The establishment of the spectrum biological databases of burn patients and presentation of the related biological data, see FIG. 15.

① The data results of cases included four parts:

a. Basic information: indicating the general information and medical history of the patient and the detailed record of the injury site, etc.; the patient having multiple burns of the body caused by a metal aluminum solution, local skin of the sacral region showed a typical carbon black change, hard texture, no obvious pain when touched.

b. Spectrum detection data: matching with the detection data according to the damage location, recording and numbering.

c. The standard photographs record of the clinical cases: reflecting the situation of lesions on admission accurately.

d. The pathological results record: sites of lesion were cut during the operation and delivered for pathological examination to obtain the results.

② The real-time detection and analysis of the wound surface of skin burn patients with different depths could be realized by the spectral detector in the near infrared band (1100 nm~2500 nm): compared with the normal skin, wound detection results of the patient in long wavelength band (1100 nm~2500 nm) indicated that the reflection spectrum curve of the skin after burn changed in the 1100 nm~2500 nm, with the extension of burn time, the characteristic amplitude at a particular peak decreased; with the increase of the depth, the curve of the area of burn center (parts marked with pink corner) becomes more flat, and the angle between the horizontal baseline becomes smaller.

③ The in vivo, real-time, non-invasive detection results of the spectrometer for application of clinical burn cases and the morphology, band and rules of the specific curve obtained during the detection of different depth of wound in visible light spectrum have the same trend.

④ In combination with the gold standard test results of the excision site of skin lesions and matched with spectral detection results again, it was finally confirmed that the diagnostic results for the burn area of lumbosacral skin of patients was third-degree burns of the central district of the wound (pink logo).

5) The normal skin spectrum biological detection database was established. The standard of wound detection and data collection strategy was set up. All the cases collection processes met with the relevant requirements of the ethics committee of Southwest Hospital and had the consent of the patients.

① Collection site: calibration principles for skin care were referred, spectral acquisition calibration points were forehead, face, upper arms, outside of neck, and the inner lower side of clavicle, repeat 3 times per site.

② Collection conditions: quiet state, supine, the target site without any strong shaking and tremble during the acquisition; fiber probe perpendicular to the target region for collection, calibration 1 cm;

③ Environmental conditions: room temperature 18-22 degrees, humidity 55%-60%, the working and light conditions inside and outside the ward during the collection of spectral information were unified;

④ Inclusion criteria: no hair, no injuries, erythema, allergies, depression, scars, acne, moles, ringworm, warts and mosquito bites and other abnormalities; no sweat and grease in the collection process, clean up if any.

⑤ Recording method: basic information of patients+real time photographs+spectral data collection. Basic information includes: ID number, name, gender, age, weight and contact information, etc.

(vii) Testing of the Clinical Detection Function of the Spectrum Imaging Instrument The spectral images of hand wound of burn patients were collected on-site by near infrared spectroscopy imaging instrument and displayed through three-dimensional color images. It could be accurately distinguish between normal tissue and burn area, and showed good functions of locating injury in burn site, determining the area of injury of burn and accurate spectral biology diagnosing. The diagnostic effect of "combination of image and spectrum" was achieved.

The invention claimed is:

1. A near-infrared spectrum imaging system for diagnosis of the depth and the area of burn skin necrosis comprising a spectrum imager and a computer controlled system, characterized in that:

the spectrum imager comprises a light source, an optical lens, a filter, a driving controller, and a CCD camera; the filter uses a wide-spectrum liquid crystal tunable filter (LCTF), which obtains spectral signals of 1100-2500 nm waveband;

the computer controlled system is internally provided with a universal module, a data module, a spectrum correction module, a spectrum matching module, and a burn wound three-dimensional synthesizing module;

the near-infrared spectrum imaging system obtains spectral image data of burn skin necrosis tissue of a target region by the spectrum imager, inputs the data into the computer controlled system, and the computer controlled system performs image analysis and processing, that is, firstly spectrum correction is performed by means of the spectrum correction module, and spectral matching and recognition is performed by means of the spectrum matching module on a spectral reflectance curve corresponding to each image pixel in an corrected spectral image and a standard spectral reflectance curve of a burn skin necrosis spectral database in a data module, the depth and the area of burn of the target region are obtained, and finally a three-dimensional image of the target region is synthesized by the burn wound three-dimensional synthesizing module and is displayed by a display device;

the standard spectral reflectance curve in a burn skin necrosis spectral database and burn depth in the pathology database have one to one matching relationship, features of the spectral reflectance curves of burn skin necrosis in 1100-2500 nm waveband are used to quantify necrotic signal of burn skin, and the necrotic signal and pathological data are correlated, so that the standard spectral reflectance curve in a burn skin necrosis spectral database is matched with burn depth in pathological database, each standard spectral curve in the burn skin necrosis spectral database represents a burn depth;

wherein, the wide-spectrum liquid crystal tunable filter (LCTF) is a multistage cascaded structure, including: a set of electronically controlled liquid crystal wave plates, a set of fixed phase retarder and a set of polarizers; the polarizers, the electronically controlled liquid crystal wave plates and the fixed phase retarders are arranged in parallel with each other, interval stacked, to form multistage.

2. The near-infrared spectrum imaging system of claim 1, characterized in that a fixed phase retarder can be set in the first stage of the multistage cascaded structure; wherein the transmitted polarized light directions of all the polarizers are parallel to each other, the fast axis directions of all electronically controlled liquid crystal wave plates and transmitted polarized light directions of all the polarizers are at an angle of 45°; the electronically controlled liquid crystal wave plates in each stage of the structure are controlled by a overvoltage drive controller which loads AC overvoltage driving signal with different amplitude.

3. The near-infrared spectrum imaging system of claim 2, characterized in that: the electronically controlled liquid crystal wave plate includes an intermediate nematic phase liquid crystal layer as well as an alignment film, a transparent conductive film, and a transparent substrate which are sequentially and symmetrically arranged on both sides, the alignment films on both sides of the nematic phase liquid crystal layer are antiparallel in the directions of friction, the liquid crystal molecules in the liquid crystal layer are arranged along the surface, the thickness of the liquid crystal layer is controlled by the transparent spacer set therein.

4. The near-infrared spectrum imaging system of claim 3, characterized in that: the LCTF drive controller is driven by overvoltage, the electronically controlled liquid crystal wave plate loads AC overvoltage driving signals with different amplitudes, an overvoltage driver is used for driving: if a liquid crystal wave plate requires a driving voltage $V_2$, firstly a narrow pulse with a short duration t is applied when driving, the value range of t is between 0-50 ms, t is not equal to zero, the voltage amplitude of $V_3 > V_2$, the amplitude range of $V_3$ is between 10-50V, and then applying $V_2$ driving voltage, the voltage amplitude is between 0-10V but not equal to zero, alternating frequency is in 0.5-5KHz.

5. The near-infrared spectrum imaging system of claim 3, characterized in that: the working band of the wide spectral liquid crystal tunable filter (LCTF) covers 900 nm~2500 nm; spectral resolution: 5-20 nm; optical transmittance: 5-30%; field of view angle: 1-10°.

6. Method for obtaining image information of burn depth and burn area of burn skin in target region by using the near-infrared spectrum imaging system of claim 1, the steps are as follows:
(1) illuminating the target region of the burn skin by the light source
(2) collecting the spectral images of the target region in 1100-2500 nm waveband by LCTF and CCD cameras, obtaining the spectral data and image data of burn skin necrosis, and inputting into the computer control system;
(3) performing image analysis and processing by the computer controlled system, that is, firstly spectrum correction is performed, then spectral matching and recognition is performed on the spectral reflectance curve corresponding to each image pixel in the corrected spectral image and the standard spectral reflectance curve in a burn skin necrosis spectral database, the depth and the area of burn of the target region are obtained, and finally a three-dimensional image of the target region is synthesized and is displayed by a display device;
the standard spectral reflectance curve in a burn skin necrosis spectral database and burn depth in the pathology database have one to one matching relationship, features of the spectral reflectance curves of burn skin necrosis in 1100-2500 nm waveband are used to quantify necrotic signal of burn skin, and the necrotic signal and pathological data are correlated, so that standard spectral reflectance curve in a burn skin necrosis spectral database is matched with burn depth in pathological database, each standard spectral curve in the burn skin necrosis spectral database represents a burn depth;
wherein, the wide-spectrum liquid crystal tunable filter (LCTF) is a multistage cascaded structure, including: a set of electronically controlled liquid crystal wave plates, a set of fixed phase retarder and a set of polarizers; the polarizers, the electronically controlled liquid crystal wave plates and the fixed phase retarders are arranged in parallel with each other, interval stacked, to form multistage.

7. The method for obtaining image information of burn depth and area of burn skin in target region of claim 6, characterized in that: features of the spectral reflectance curves of burn skin necrosis in 1100-2500 nm waveband include shape of the spectral reflectance curve, average amplitude of the curve, and the amplitude difference between peaks and valleys in the curves.

8. The method for obtaining image information of burn depth and area of burn skin in target region by using the near-infrared spectrum imaging system of claim 7, characterized in that: the specific process of the step (3) is as follows:
(3.1) spectrum correction: the amplitude of spectrum curve corresponding to each image pixel of the spectral image in the original spectral image of the target region is divided by the amplitude of spectral curve corresponding to the image pixel of the spectral image of the white board in the same condition so as to remove the influence of the background light and the heterogeneity of the light source, and the spectral reflectance curve of the target region is obtained;
(3.2) spectral matching and identifying: performing comparative analysis of spectral reflectance curve of each pixel in the spectral image of the target region after the correction with the standard spectral reflectance curve of the burn and necrotic skin spectral database, that is, matching and identifying the skin reflectance spectra curve of known burn depth with spectral reflectance curve of target region, and calculating the similarity value between the spectral reflectance curve of the image pixel in the target region and standard spectral reflectance of skin with different burn depth, the burn depth corresponding to the maximum similarity value is taken as the burn depth of the image pixel of the target region, then each image pixel in the target region is identified by matching, and the burn depth and area of the target region are obtained;
(3.3) spectral image synthesis and display: three dimensional syntheses and display of the data of burn depth and burn area of the target region.

9. The near-infrared spectrum imaging system for diagnosis of the depth and the area of burn skin necrosis of claim 1, characterized in that features of the spectral reflectance curves of burn skin necrosis in 1100-2500 nm waveband include shape of the spectral reflectance curve, average amplitude of the curve, and the amplitude difference between peaks and valleys in the curves.

10. The near-infrared spectrum imaging system claim 1, characterized in that: the light source provides a coaxial or nearly coaxial illumination source, and the spectral range of the illumination source covers 900-2500 nm, and the illumination of target region is uniform or nearly uniform.

11. The near-infrared spectrum imaging system claim 1, characterized in that the computer control system comprises:
universal module, which controls the on and off of the light source, power rationing for each part of the hardware in the spectral imager, as well as various ports and interfaces of the system;
data module, including the burn skin necrosis spectral database and burn skin necrosis pathology database; the wave band of the spectral reflectance curve in the burn skin necrosis spectral database is 1100-2500 nm, sources of the spectral reflectance curve data include fiber spectrometer and medical imaging spectrometer; the spectral reflectance curve in the burn skin necrosis spectral database and the burn depth in the burn skin necrosis pathology database have a one to one matching relationship, that is, the spectral reflectance curve can be used to represent the depth of burn;
spectrum correction module, wherein amplitude of spectrum curve corresponding to each image pixel of the spectral image in the original spectral image of the target region is divided by the amplitude of spectral curve corresponding to image pixel of the spectral image of the white board in the same condition so as to remove the influence of the background light and the heterogeneity of the light source, and the spectral reflectance curve of the target region is obtained;
spectral matching module, which is used for comparative analysis of spectral reflectance curve of each image pixel in the spectral image of the target region after the correction with the standard spectral reflectance curve of the burn and necrotic skin spectral database, that is, matching and identifying the skin reflectance spectra curve of known burn depth with spectral reflectance curve of target region, and calculating the similarity value between the spectral reflectance curve of the pixel in the target region and the standard spectral reflectance of skin with different burn depth, the burn depth corresponding to the maximum similarity value is taken as the burn depth of the target region image pixel, then each image pixel in the target region is identified by matching, and the burn depth and area of the target region were obtained;

three dimensional synthesis module of burn wound, which is used for three dimensional synthesis and display of the data of burn depth and burn area of the target region.

\* \* \* \* \*